United States Patent
Smith

(10) Patent No.: US 11,596,401 B2
(45) Date of Patent: Mar. 7, 2023

(54) POSTIONING METHOD FOR STAPLER WITH COMPLIANT TIP

(71) Applicant: Intuitive Surgical Operations, Inc., Sunnyvale, CA (US)

(72) Inventor: Jeffrey A. Smith, Petaluma, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 57 days.

(21) Appl. No.: 17/213,158

(22) Filed: Mar. 25, 2021

(65) Prior Publication Data

US 2021/0282775 A1  Sep. 16, 2021

Related U.S. Application Data

(63) Continuation of application No. 15/772,529, filed as application No. PCT/US2016/059646 on Oct. 31, 2016, now abandoned.

(60) Provisional application No. 62/255,138, filed on Nov. 13, 2015.

(51) Int. Cl.
| | |
|---|---|
| *A61B 17/072* | (2006.01) |
| *A61B 34/37* | (2016.01) |
| *A61B 34/30* | (2016.01) |
| *A61B 90/00* | (2016.01) |

(52) U.S. Cl.
CPC ........ *A61B 17/07207* (2013.01); *A61B 34/30* (2016.02); *A61B 34/37* (2016.02); *A61B 2017/07257* (2013.01); *A61B 2034/305* (2016.02); *A61B 2090/0807* (2016.02); *A61B 2090/08021* (2016.02)

(58) Field of Classification Search
CPC ............ A61B 17/072; A61B 17/07207; A61B 2017/08221; A61B 2017/08271; A61B 2017/07257; A61B 34/30; A61B 34/37; A61B 2034/305; A61B 2090/0807; A61B 2090/08021
USPC ........................................... 227/175.1–182.1
See application file for complete search history.

(56) References Cited

U.S. PATENT DOCUMENTS

| | | | |
|---|---|---|---|
| 2,887,111 A * | 5/1959 | Leyro | A61B 17/282 |
| | | | 606/148 |
| 4,633,861 A | 1/1987 | Chow et al. | |
| 8,136,711 B2 * | 3/2012 | Beardsley | A61B 17/07207 |
| | | | 227/176.1 |
| 8,398,653 B2 | 3/2013 | White et al. | |
| 8,403,196 B2 | 3/2013 | Beardsley et al. | |
| 10,786,252 B2 * | 9/2020 | Harris | A61B 17/072 |

(Continued)

OTHER PUBLICATIONS

International Search Report and Written Opinion for Application No. PCT/US2016/059646, dated Feb. 16, 2017, 15 pages (ISRG07240/PCT).

(Continued)

*Primary Examiner* — Anna K Kinsaul
*Assistant Examiner* — Himchan Song
(74) *Attorney, Agent, or Firm* — Schwegman Lundberg & Woessner, P.A.

(57) ABSTRACT

A surgical stapler is provided that includes a first jaw and a second jaw. The first jaw includes a proximal end portion and a distal end portion. The second jaw includes a proximal end portion and a distal end portion. The proximal end portion of the first jaw is pivotally mounted to the proximal end portion of the second jaw. A flexible guide is secured to the distal end portion of the first jaw.

13 Claims, 14 Drawing Sheets

(56) References Cited

U.S. PATENT DOCUMENTS

| | | |
|---|---|---|
| 2004/0243151 A1 | 12/2004 | Demmy et al. |
| 2007/0114261 A1 | 5/2007 | Ortiz et al. |
| 2008/0169330 A1 | 7/2008 | Shelton et al. |
| 2008/0269793 A1 | 10/2008 | Scirica et al. |
| 2011/0226837 A1 | 9/2011 | Baxter, III et al. |
| 2012/0241492 A1* | 9/2012 | Shelton, IV ...... A61B 17/00491 227/175.1 |
| 2012/0248167 A1* | 10/2012 | Flanagan ............. A61B 17/072 227/2 |
| 2014/0239042 A1 | 8/2014 | Simms et al. |
| 2014/0263572 A1 | 9/2014 | Shelton, IV et al. |
| 2015/0209030 A1 | 7/2015 | Kostrzewski et al. |
| 2015/0209037 A1 | 7/2015 | Kostrzewski et al. |
| 2017/0224343 A1 | 8/2017 | Baxter, III et al. |
| 2018/0235609 A1* | 8/2018 | Harris .............. A61B 17/07207 |
| 2018/0325514 A1* | 11/2018 | Harris ................. A61B 17/072 |
| 2018/0325515 A1* | 11/2018 | Harris ................ A61B 17/2909 |
| 2019/0076143 A1 | 3/2019 | Smith |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

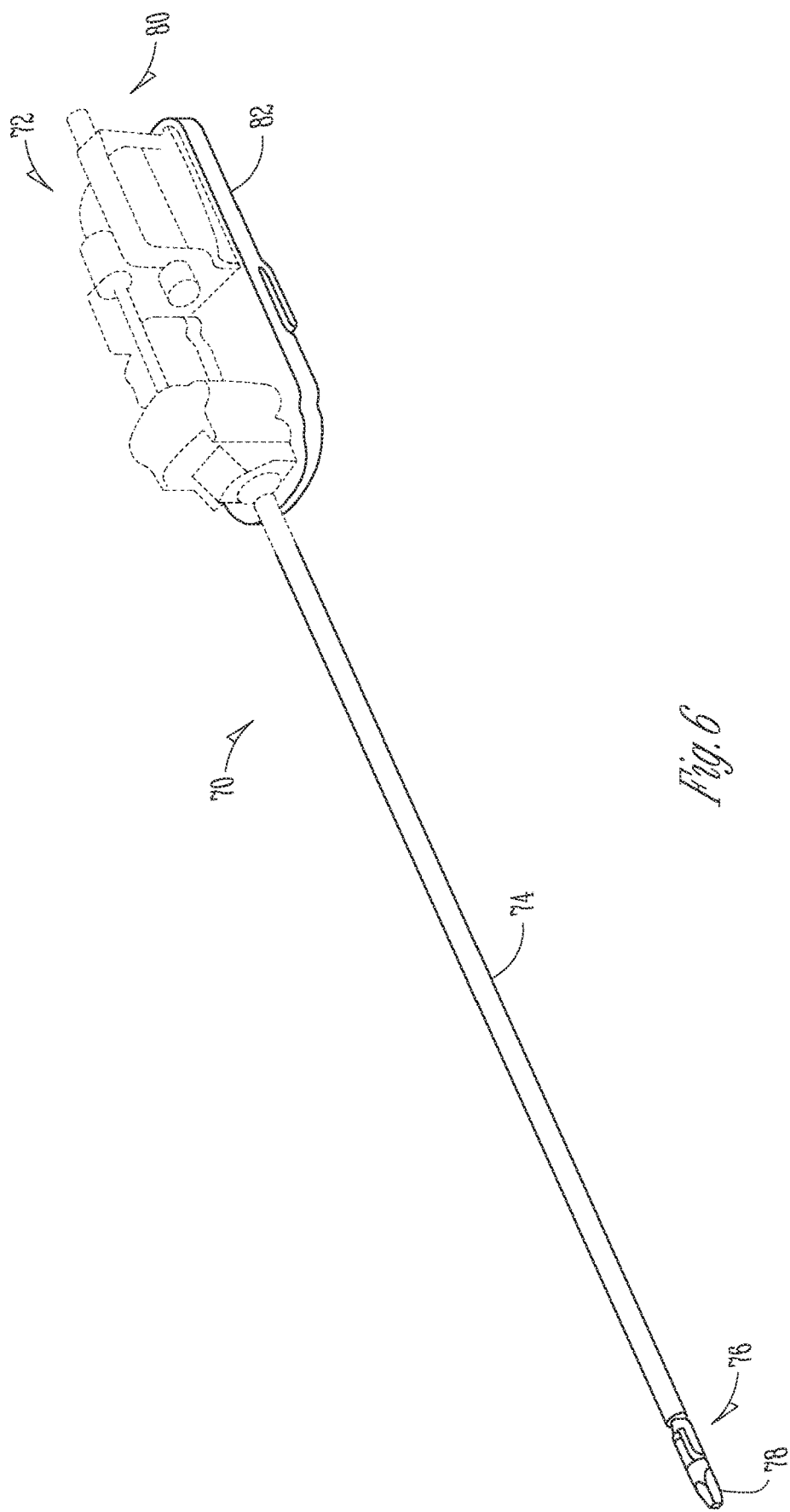

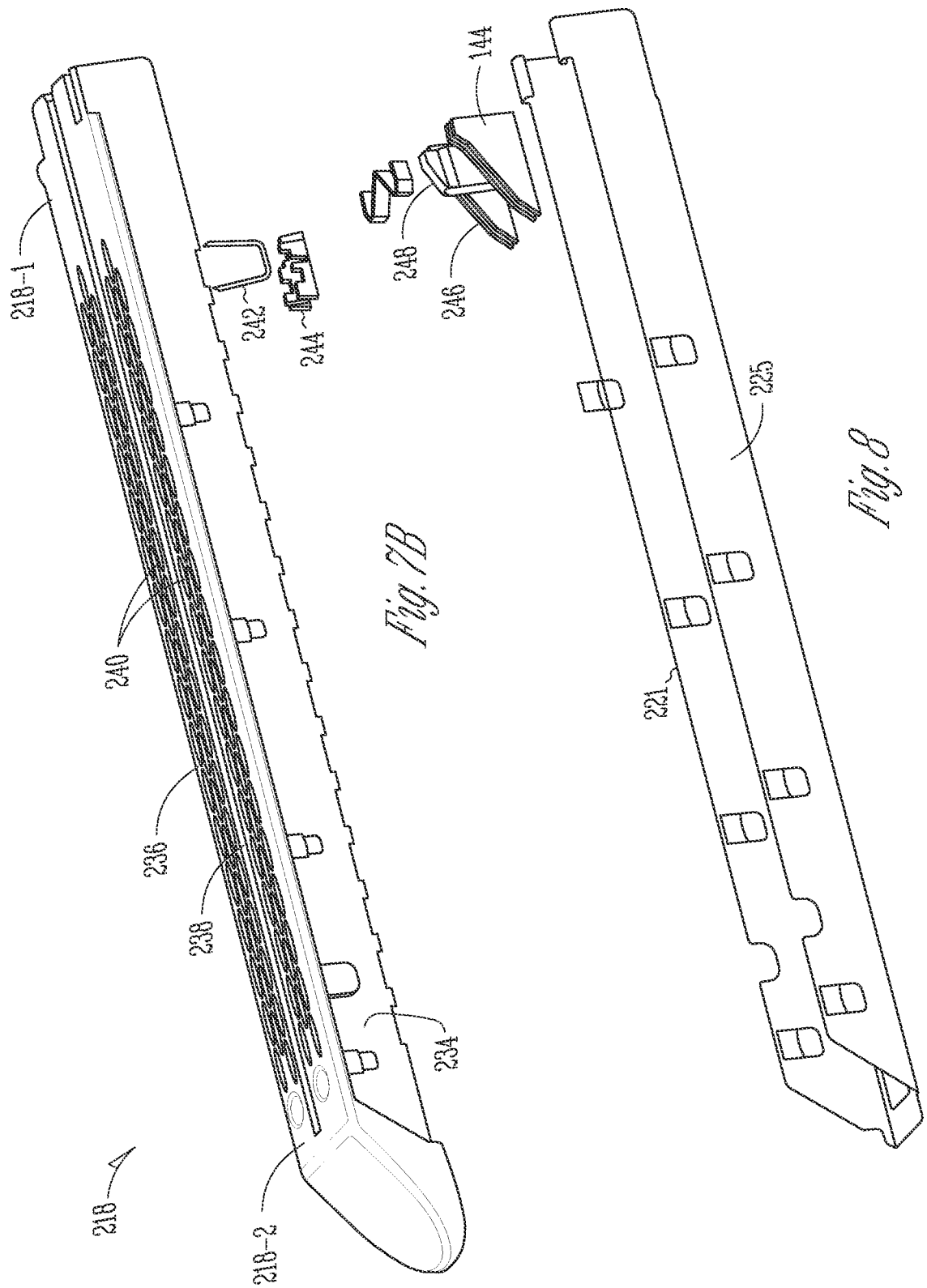

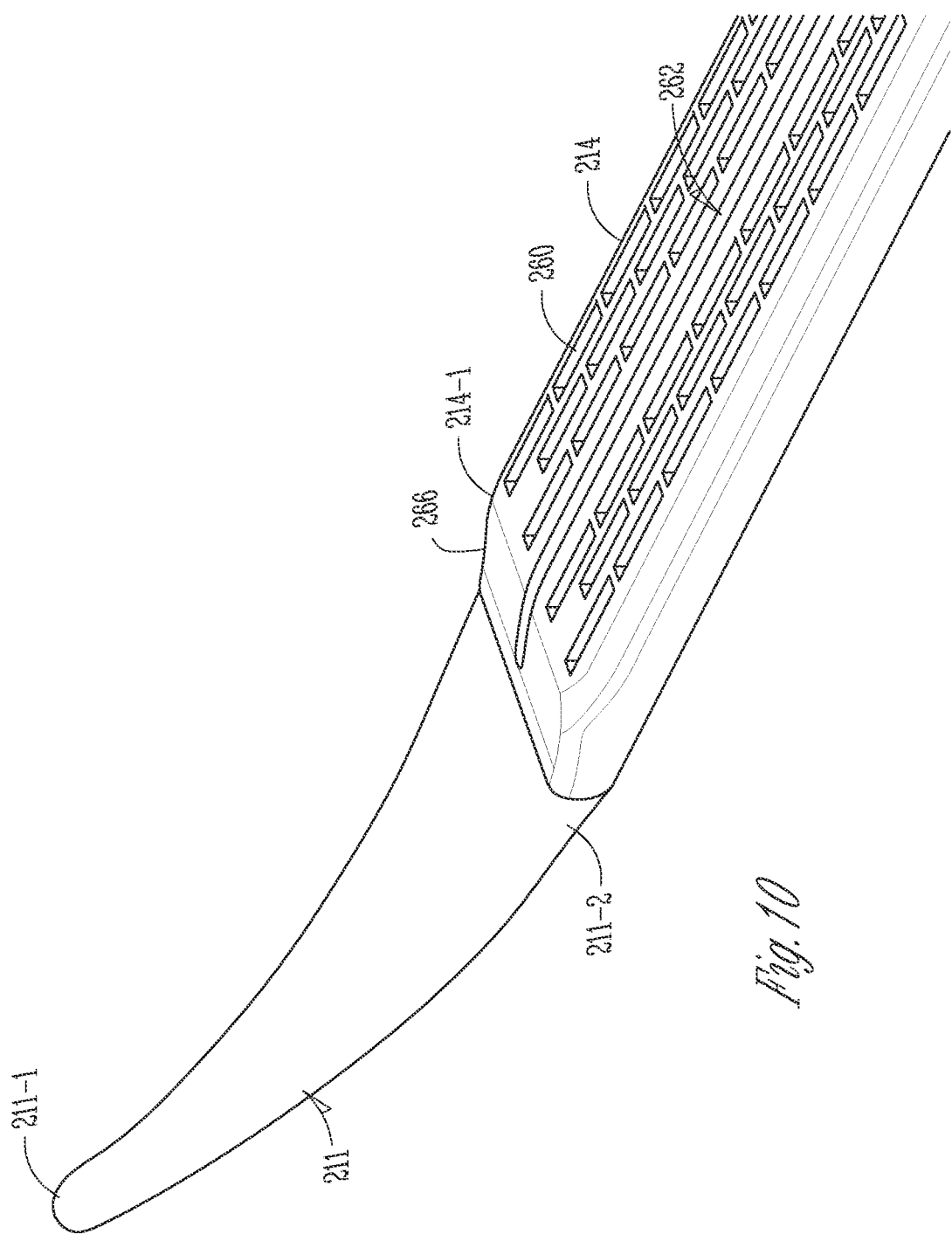

*Fig. 13A*
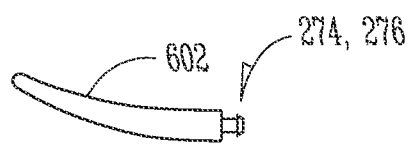
*Fig. 13B*
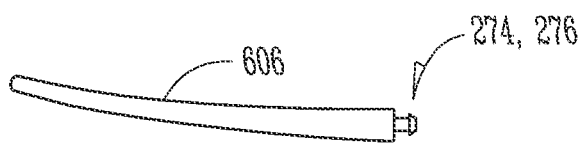
*Fig. 13C*
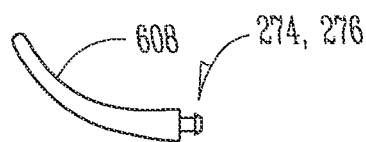 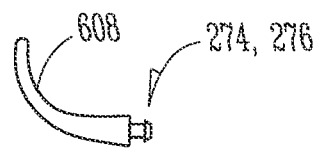
*Fig. 13D*  *Fig. 13E*

POSTIONING METHOD FOR STAPLER WITH COMPLIANT TIP

RELATED APPLICATIONS

This patent application is a continuation of and claims the benefit of priority under 35 U.S.C. § 120 to U.S. patent application Ser. No. 15/772,529, filed on Apr. 30, 3018, which is a U.S. National Stage Filing tinder 35 U.S.C. 371 from International Application No. PCT/US2016/059646, filed on Oct. 31, 2016, and published as WO 2017/083129 A1 on May 18, 2017, which claims priority to and the benefit of the filing date ofIUS Provisional Patent Application 62/255,138, entitled "STAPLER ANVIL WITH COMPLIANT TIP" filed Nov. 13, 2015, each of which is incorporated by reference herein in its entirety.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

Minimally invasive teleoperated surgical systems have been developed to increase a surgeon's dexterity when working on an internal surgical site, as well as to allow a surgeon to operate on a patient from a remote location (outside the sterile field). In a teleoperated surgical system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the teleoperated surgical system can provide mechanical actuation and control of a variety of surgical instruments or tools having end effectors that perform various functions for the surgeon, for example, holding or driving a needle, grasping a blood vessel, dissecting tissue, stapling tissue, or the like, in response to manipulation of the master input devices.

SUMMARY

In one aspect, a surgical stapler includes a first jaw that includes a proximal end portion and a distal end portion and a second jaw that includes a proximal end portion and a distal end portion. The proximal end portion of the first jaw is pivotally mounted to the proximal end portion of the second jaw. The flexible guide secured to the distal end portion of the first jaw.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 6 is an illustrative drawing showing an example surgical tool in accordance with some embodiments.

FIG. 7B is an illustrative side view of the distal portion of the surgical tool assembly with the stapling device jaws in a closed position in accordance with some embodiments.

FIG. 8 is an illustrative exploded view of a detachable stationary second jaw in accordance with some embodiments.

FIG. 10 is an illustrative perspective view of a flexible guide secured to the distal end of the first jaw, in accordance with some embodiments.

FIGS. 13A-13E are illustrative drawings of multiple alternative flexible guide tips having different contours that may be interchangeably secured to a far distal end portion of a first jaw in accordance with some embodiments.

DESCRIPTION OF EMBODIMENTS

Figure 1:
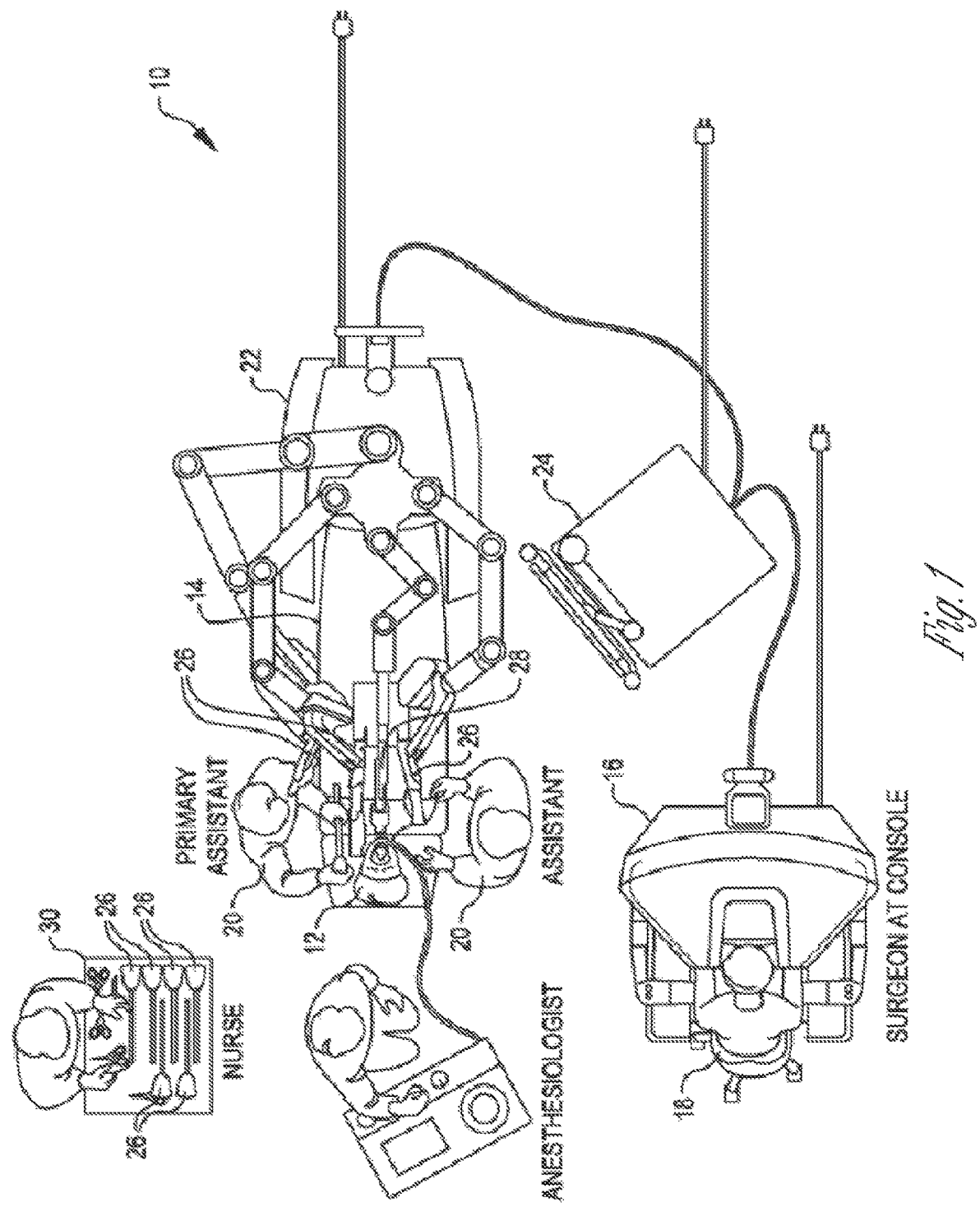
FIG. 1 is an illustrative plan view illustration of a teleoperated surgical system in accordance with some embodiments.

The following description is presented to enable any person skilled in the art to create and use a stapler anvil with compliant tip for use in surgery. Various modifications to the embodiments will be readily apparent to those skilled in the art, and the generic principles defined herein may be applied to other embodiments and applications without departing from the spirit and scope of the inventive subject matter. Moreover, in the following description, numerous details are set forth for the purpose of explanation. However, one of ordinary skill in the art will realize that the inventive subject matter might be practiced without the use of these specific details. In other instances, well-known machine components, processes and data structures are shown in block diagram form in order not to obscure the disclosure with unnecessary detail. Identical reference numerals may be used to represent different views of the same item in different drawings. Flow diagrams in drawings referenced below are used to represent processes. A computer system may be configured to perform some of these processes. Modules within flow diagrams representing computer implemented processes represent the configuration of a computer system according to computer program code to perform the acts described with reference to these modules. Thus, the inventive subject matter is not intended to be limited to the embodiments shown, but is to be accorded the widest scope consistent with the principles and features disclosed herein.

Referring now to the drawings, in which like reference numerals represent like parts throughout the several views, FIG. 1 is an illustrative plan view of a teleoperated surgical system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The teleoperated surgical system 10 can further include a Patient Side Cart 22 and an Electronics Cart 24. The Patient Side Cart 22 can manipulate at least one removably coupled tool assembly 26 (hereinafter also referred to as a "tool") through a minimally invasive incision in the body of the Patient 12 while the Surgeon 18 views the surgical site through the Console 16. An image of the surgical site can be obtained by an imaging device 28 (also called endoscope 28 in contexts where endoscopes may be used), such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors.

Figure 2:
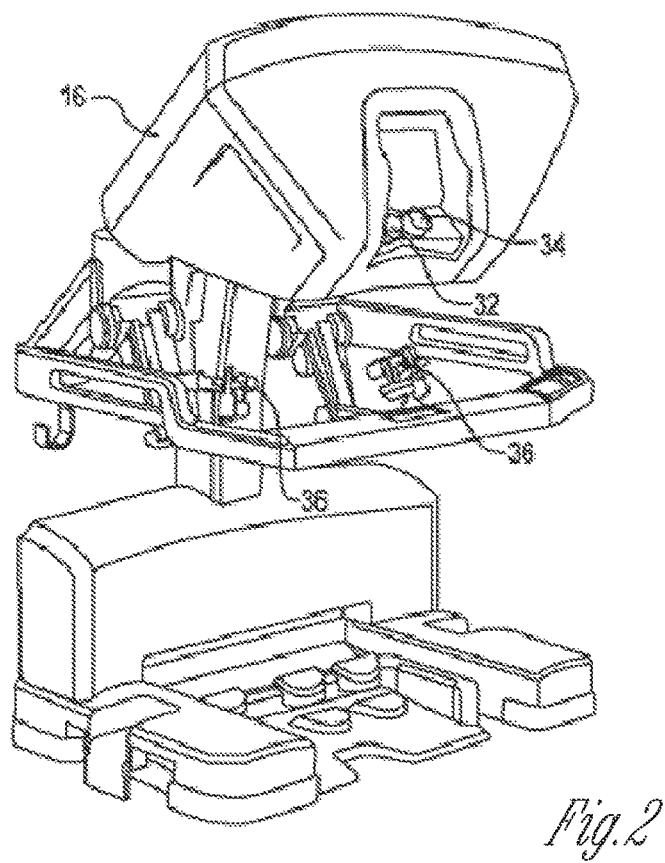
FIG. 2 is an illustrative perspective view of the Surgeon's Console in accordance with some embodiments.

FIG. 2 is an illustrative perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

Figure 3:
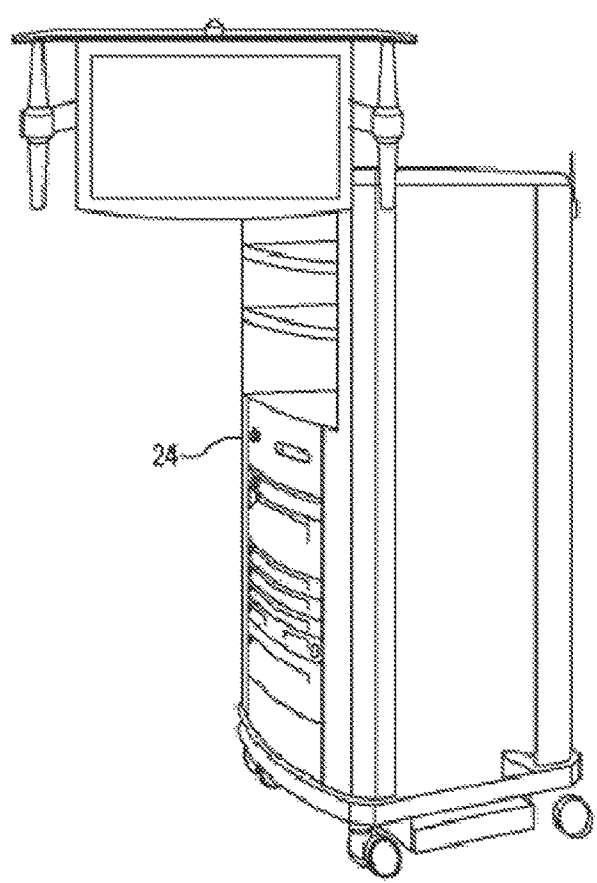
FIG. 3 is an illustrative perspective view of the Electronics Cart in accordance with some embodiments.

FIG. 3 is an illustrative perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope.

Figure 4:
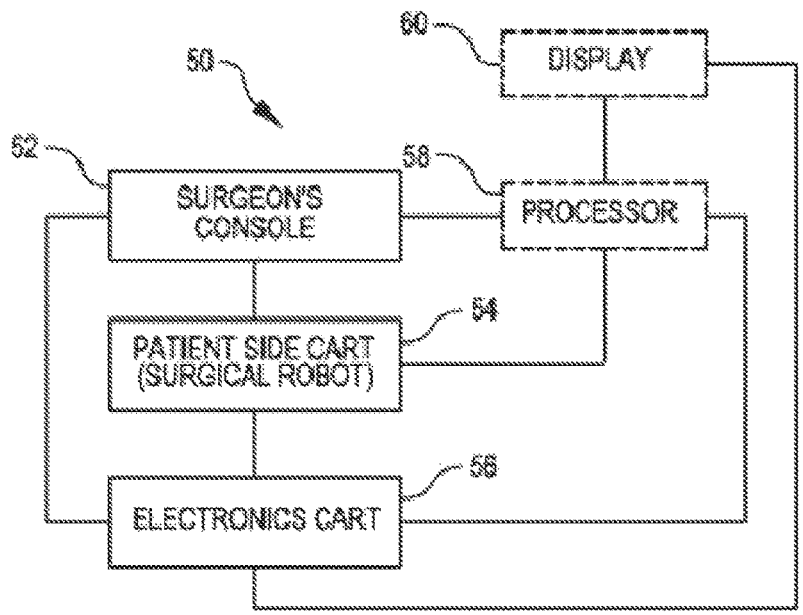
FIG. 4 is an illustrative bock diagram diagrammatically representing functional relationships among components of a teleoperated surgery system in accordance with some embodiments.

FIG. 4 is an illustrative bock diagram diagrammatically representing functional relationships among components of a teleoperated surgery system 50 (such as system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5A:
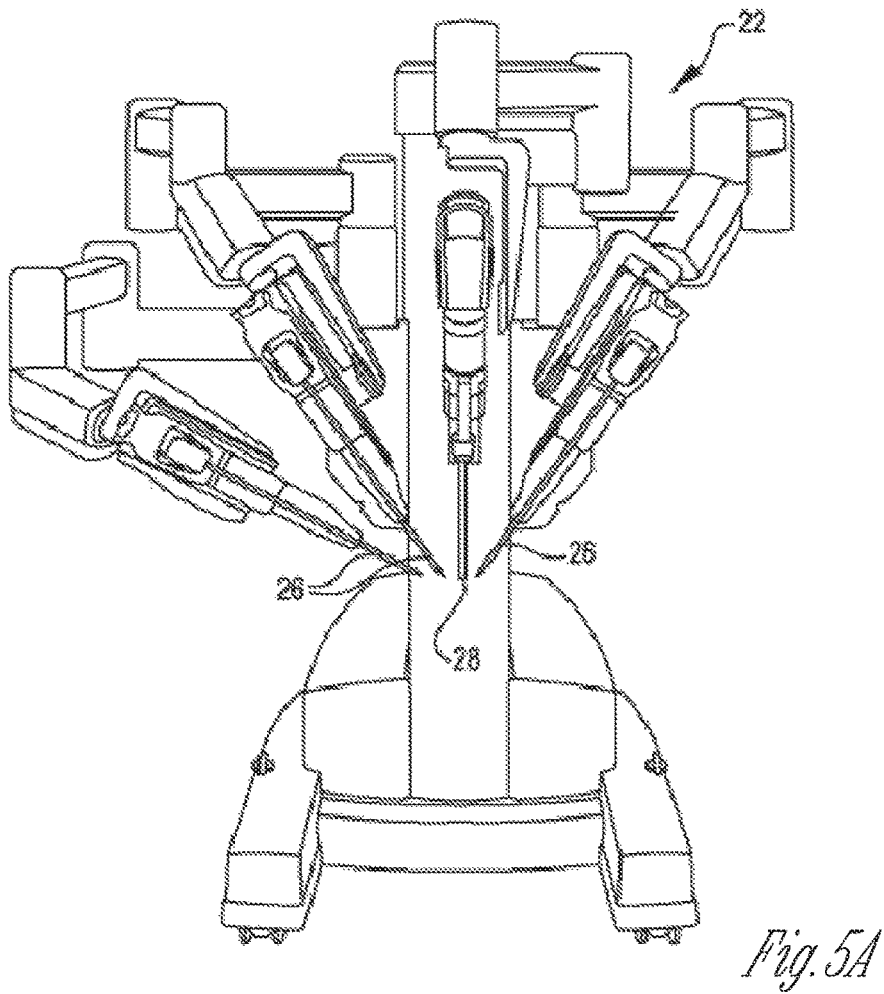
FIGS. 5A-5B are illustrative drawings showing a Patient Side Cart and a surgical tool 62, respectively in accordance with some embodiments.
Figure 5B:
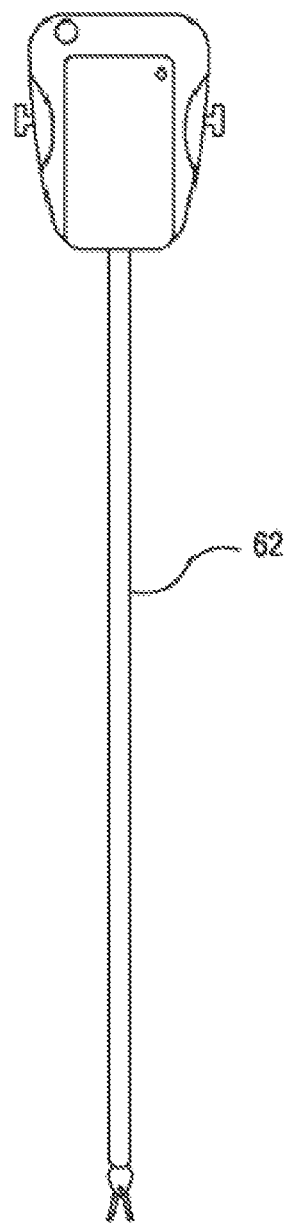

FIGS. 5A-5B are illustrative drawings showing a Patient Side Cart 22 and a surgical tool 62, respectively in accordance with some embodiments. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by teleoperated mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

FIG. 6 is an illustrative drawing showing an example surgical tool 70 that includes a proximal chassis 72, an instrument shaft 74, and a distal end effector 76 having a jaw 78 that can be articulated to grip a patient tissue. The proximal chassis includes input couplers that are configured to interface with and be driven by corresponding output couplers of the Patient Side Cart 22. The input couplers are drivingly coupled with drive shafts that are disposed within the instrument shaft 74. The drive shafts are drivingly coupled with the end effector 76.

Figure 7A:
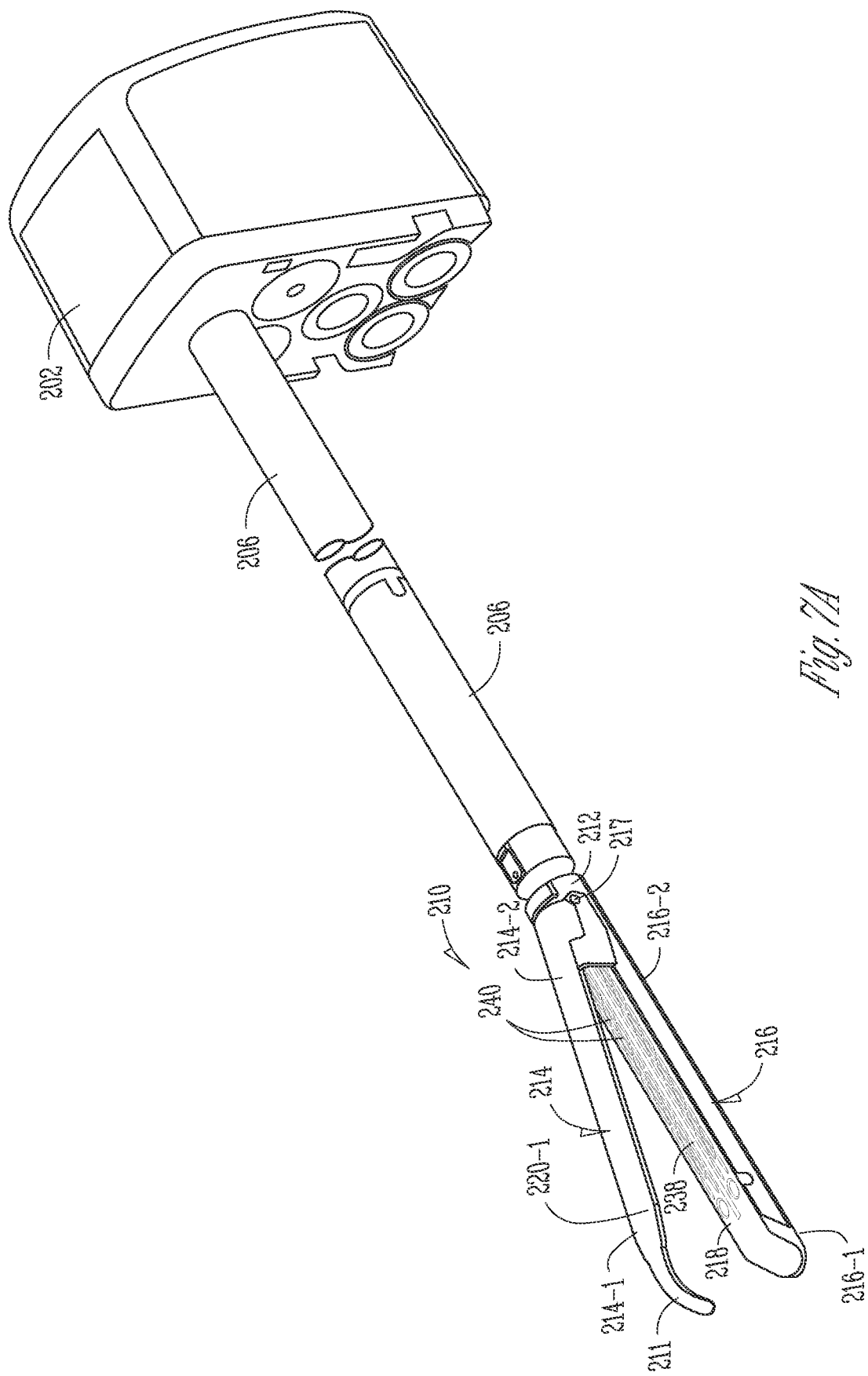
FIG. 7A is an illustrative perspective drawing of a surgical tool assembly with a stapling device having first and second jaws and having a compliant guide tip secured to the first jaw in accordance with some embodiments.

FIG. 7A is an illustrative perspective drawing of a surgical tool assembly 200 with a stapling device 210 (also "stapler device 210") having a compliant guide (also called flexible guide) 211 disposed at a distal end in accordance with some embodiments. The stapling device includes rigid first and second jaws 214, 216 shown in an open position. The compliant guide 211 is secured to the first jaw 214 of the stapling device 210 to aid a surgeon in guiding the first jaw 214 to an anatomical tissue structure that is to be stapled that is located behind other anatomical features that obscures the tissue structure from a surgeon's view. The tool assembly 200 includes a proximal actuation assembly 202, a main shaft 206, a two degree of freedom (2-dof) wrist 208, shown in partial cutaway, and the stapling device 210. The stapling device 210 includes an end effector base 212 coupled to a distal side of the 2-dof wrist 208, a first articulable jaw 214 and a stationary second jaw 216. The first jaw 214, sometimes referred to as the anvil jaw 214, has a distal end 214-1 and a proximal end 214-2. The second jaw 216 also has a distal end 216-1 and a proximal end 216-2. The end effector base 212 includes a pivot pin 217 secured between the end effector base 212 and a proximal end of the first jaw 214, about which a proximal end of the first jaw 214 pivots to achieve opening and closing movement of the first jaw 214 relative to the second jaw 216. In an open position shown in FIG. 7A, the first jaw 214 is rotated to a position in which distal ends 214-1, 216-1 of the first and second jaws 214, 216 are spaced apart so that the jaws can be more easily maneuvered within a surgical site to encompass anatomical tissue (not shown) between them without actually clamping the tissue in place between them.

In many embodiments, the actuation assembly 202 is operatively coupled with the wrist 208 so as to selectively reorient the stapling device 210 relative to the main shaft 206 in two dimensions, referred to as pitch and yaw, and is operatively coupled with the stapling device 210 so as to actuate rotation of the first jaw 214 about the pivot pin 217 to open and close the first jaw 214 relative to the end effector base 212 and the second jaw 216. In accordance with some embodiments, control cables (not shown) extend through a bore in the main shaft 206 to interconnect the actuation assembly 202 with the wrist 208. The actuation assembly 202 imparts forces to the control cables that result in pitch and yaw movement of the wrist 208 and the stapler device 210. Details of a suitable cable control mechanisms that can be used are disclosed in U.S. Pat. No. 8,852,174 (filed Nov. 12, 2010) issued to Burbank, which is expressly incorporated herein in its entirety by this reference. In accordance with some embodiments a rotationally-driven clamping mechanism (not shown) actuates the upper jaw 214 relative to the lower jaw 216 to securely clamp tissue between the upper and lower jaws. The clamping mechanism is rotationally driven by a drive shaft (not shown) disposed internal to the main shaft 206. Details of a suitable drive shaft-driven clamping mechanism that can be used are disclosed in U.S. Pat. No. 8,876,857 issued to Burbank (filed Nov. 12, 2010), the full disclosure of which is hereby expressly incorporated herein by reference. In alternative embodiments, suitable cables (not shown) are used to impart forces to open or close the jaws 214, 216. Details of a suitable cable-driven clamping mechanism that can be used are disclosed U.S. Patent Application Ser. No. 62/255,123, filed on Nov. 13, 2015 and entitled "Stapler with composite cardan and screw drive,", the full disclosure of which is hereby expressly incorporated herein by reference.

FIG. 7B is an illustrative side view of the distal portion of the surgical tool assembly 200 with the jaws 214, 216 in a closed position disposed parallel to each other spaced apart by an amount to accommodate anatomical tissue (not shown) that may be clamped between them in accordance with some embodiments. The first jaw 214 includes an anvil 220 having a rigid metal anvil surface 220-1 that faces the second jaw 216. In operation, staples are deformed against the anvil surface 220-1 to staple together tissue (not shown) disposed between the first and second jaws 214, 216. The second jaw 216 includes an elongated stapler cartridge body 218 seated within a rigid metal stapler cartridge body support channel 221 configured to support the cartridge body 218. The stapler cartridge body 218 carries staples to be used to attach tissue during a surgical procedure. The stapler cartridge body 218 defines a central longitudinal knife slot 238 that extends through the cartridge body 218 and extends along substantially its entire length. The stapler cartridge body 218 also defines multiple laterally spaced rows of staple openings 106 that each extends longitudinally along the cartridge body 218. In some embodiments, three rows of staple openings 106 extended along one side of the knife slot 238, and three rows of staple openings extended along an opposite side of the knife slot 238. Each staple retention slot 240 (also "staple opening 240") is sized to receive a staple.

FIG. 8 is an illustrative exploded view of a stationary second jaw 216 in accordance with some embodiments. The second jaw 216 includes the cartridge body 218 received within a support channel structure 221. The cartridge body 218 includes a proximal end 218-1 and a distal end 218-2. The cartridge body 218 includes cartridge outer sidewalls 234 and an upper surface 236. The upper surface 236 faces the anvil 220-1 of the first jaw 214, which acts as an anvil, when the second jaw is mounted to the end effector base 212. The upper surface 236 of the cartridge 218 defines a central first longitudinal cartridge slot 238 that extends through the cartridge 218 when the cartridge body 218 is disposed within the support channel structure 221. The upper surface 236 also defines multiple rows of laterally spaced staple retention slots 240 that extend longitudinally along one side of the first cartridge slot 238 and defines multiple rows of laterally spaced staple retention slots 240 that extend longitudinally along an opposite side of the first cartridge slot 238. Each staple retention slot 240 is sized to receive a staple 242. A drive shuttle 144 includes a plurality of inclined upstanding cam wedges 246 and a knife 248 upstanding between and proximal to the cam wedges 246. The cartridge body 218 defines longitudinal slots (not shown) in its underside along which the cam wedges 246 can slide with the knife upstanding from and sliding within the first cartridge slot 238.

Figure 9A:
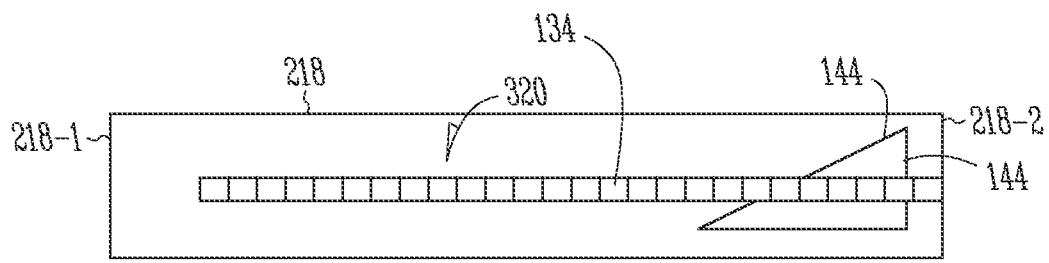
FIGS. 9A-9C are illustrative drawings showing positions of the driver shuttle within the cartridge body during different stages of staple deployment process in accordance with some embodiments.
Figure 9B:
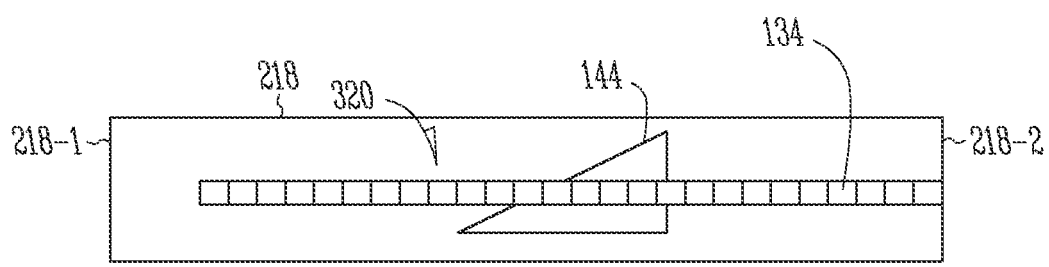
Figure 9C:
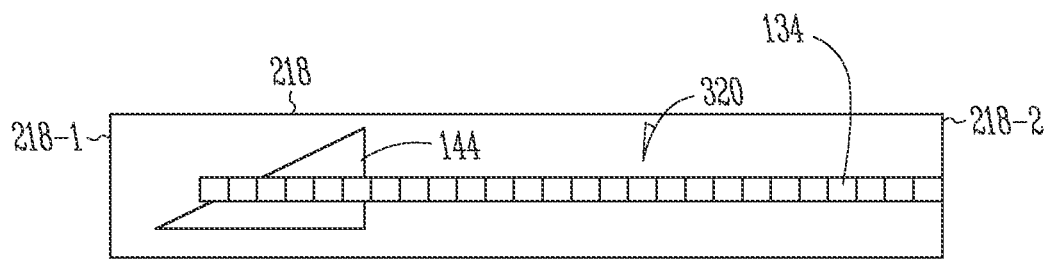

FIGS. 9A-9C are illustrative drawings showing positions of the drive shuttle 144 within the cartridge body 218 during different stages of staple deployment process in accordance with some embodiments. The cartridge body 218 defines an internal central cavity 320 extending between its distal end 218-1 and its proximal end 218-2. A lead screw 134 is mounted within the cavity 320 in engagement with complementary threads (not shown) located at the drive shuttle 144 for rotation relative to the housing cartridge body 218 and extends between the distal end 218-1 and its proximal end 218-2 through the central cavity 620.

FIG. 9A shows the drive shuttle 144 located adjacent the proximal end 218-2 of the cartridge body 218 at the beginning of a stapling run. FIG. 9B shows the drive shuttle 144 disposed in a middle portion of the cartridge body 218 during a stapling run. FIG. 9C shows the drive shuttle 144 located adjacent the distal end 218-2 after stapling completion of a stapling run. In operation during a stapling run using the stapler device 210, the drive shuttle 144 translates through the longitudinal pusher slots 239-1, 239-2, formed in an underside of the cartridge 218 to advance the cam wedges 246 into sequential contact with drive shuttle 144 within the longitudinally spaced retention slots 240, to cause drive shuttle 144 to translate vertically within retention slots 240, and to urge staples 242 from retention slots 240 into the staple deforming cavities (not shown) formed within the anvil 220 of the first jaw 214. As the drive shuttle 144 translates longitudinally, it pushes up fasteners staples, which are deformation against the anvil 220. Meanwhile, the knife 248 upstands through the first cartridge slot 238 and cuts tissue between tissue regions stapled through action of the cam wedges 246, fasteners staples and the anvil 220. U.S. Pat. No. 8,991,678 (filed Oct. 26, 2012) issued to Wellman et al., which is incorporated herein in its entirety by this reference, discloses a surgical stapler cartridge and its operation.

FIG. 10 is an illustrative perspective view of a flexible guide 211 secured to the distal end 214-1 of the first jaw 214, in accordance with some embodiments. The distal end of the first jaw includes a far distal portion 266. The anvil surface 220-1 includes multiple rows of staple deformation indents 260 configured to have staples deflected against them during dispensing of the staples 242. The far distal portion 266 of the first jaw 214 is disposed distal to the portion of the first jaw 214 in which the indents 260 are formed. The indents 260 are positioned to align with staple openings 240 formed in the cartridge body 218, when the staple device 210 jaws 214, 216 are disposed in a closed position parallel to one another. In accordance with some embodiments, the anvil surface 220-1 includes a centerline region 262 with three rows of indents 260 on each side of it. The three rows of indents 260 are aligned with three rows of staple openings 240 formed on opposite sides of the knife slot 238 when the jaws are closed. Thus, it will be appreciated that the distal end 214-1 is wide enough to accommodate the multiple rows of deformation indents 260. The flexible guide 211 includes a proximal base portion 211-2 secured to the distal end 214-1 of the first jaw 214 and includes a distal tip portion 211-1. The flexible guide 211 has a tapered shape that is wider at its proximal base 211-2 and narrower at its distal tip 211-1. The flexible guide 211 and the distal end 214-1 of the first jaw 214 have complementary outer surface contours that cooperate to provide a continuous smooth surface that includes the surface of the far distal portion 266 and the outer surface of the flexible guide 211.

Figure 11A:
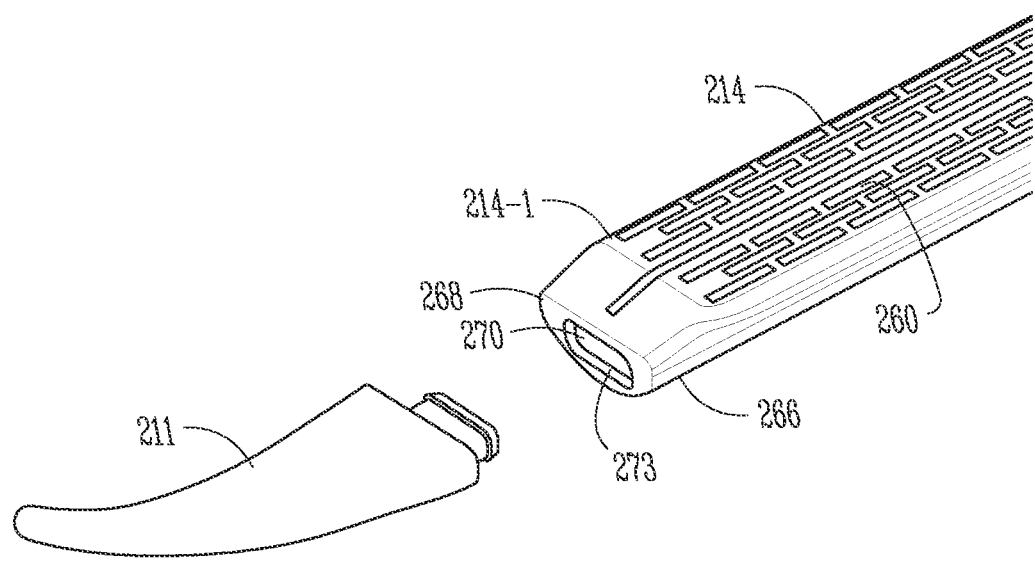
FIGS. 11A-11B are illustrative drawings showing complementary attachment mechanisms formed in the far distal portion of the first jaw (FIG. 11A) and in the proximal base portion (FIG. 11B) of the flexible guide in accordance with some embodiments.
Figure 11B:
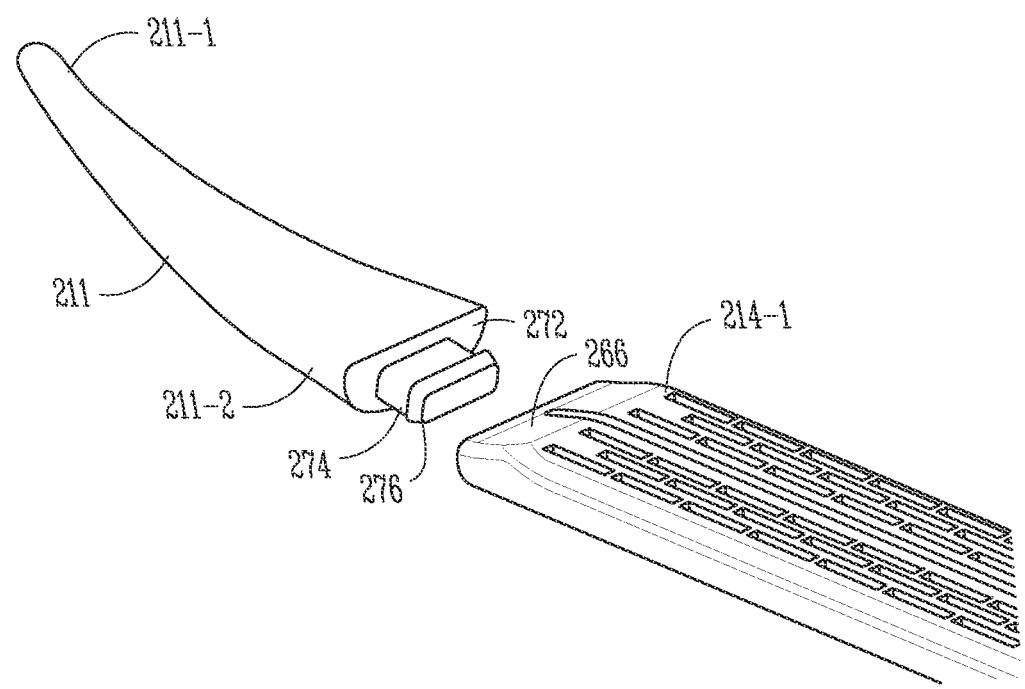

FIGS. 11A-11B are illustrative drawings showing complementary attachment mechanisms formed in the far distal portion 266 of the first jaw 214 (FIG. 11A) and in the proximal base portion 211-2 (FIG. 11B) of the flexible guide 211 in accordance with some embodiments. Referring to FIG. 11A, the far distal portion 266 of the first jaw 214 includes a substantially rectangular distal end face 268 that defines an end face opening 270 surrounded by a retainer surface 273 (in this case, also a "proximal end face 273"). Referring to FIG. 11B, the proximal base portion 211-2 of the flexible guide 211 includes a substantially rectangular proximal end face 272. A beam 274 upstands proximally from the proximal end face 272. The beam 274 includes an outward projecting flange 276. The end face opening 270 is sized to permit passage of the flange 276 through it. More particularly, the beam 274 and its flange 276 are formed of a flexible material that is sufficiently deformable for the flange 276 to be pushed through the end face opening 270. Moreover, the retainer surface 272 and the flange 276 have complementary surfaces that interact to secure the guide 211 in place once the flange 276 is received within the end face opening 270. Thus, to secure the guide 211 to the first jaw 214, a user may apply a force to push the flange 276 to deform it sufficiently to squeeze through the end face opening 270 so that the flange 276 engages the retainer surface 273. Conversely, a user may apply a force to pull the flange 276 out of engagement with the retainer surface 273 so that the upstanding bean 274 and the flange 276 can be removed through the end face opening 270.

The flexible guide 211 is used by a surgeon working manually or using a teleoperated minimally invasive surgical system to guide the first jaw 214, also referred to as the anvil jaw, of a stapler device 210 into a position in which the first and second jaws 214-216 can be closed to clamp anatomical tissue between them for stapling. The flexible guide 211 has a tapered contour that smoothly changes over its length between a small-dimension distal tip portion 211-1 and a greater dimension proximal base portion 211-2 that matches the dimension of the far distal portion 266 of the first jaw 214. The taper contour of the flexible guide 211 aids a surgeon in using the flexible guide to locate an unseen passage between anatomical structures that the first jaw 214, which is secured to the flexible guide 211, can follow.

In accordance with some embodiments, the flexible tip 211 is formed from a material that is sufficiently compliant so that the flexible guide 211 flexes in response to abutting against delicate anatomical tissue likely to be encountered in the course of its passage unseen by a surgeon behind other anatomical structures. In accordance with some embodiments, the material is sufficiently compliant that it is likely to comply with and conform to the contour of such anatomical structures so as to avoid deforming their shape and possibly causing damage likely to be encountered while the tip is out of view of a surgeon guiding the tip due to passage of the guide 211 behind other anatomical structures.

More specifically, in accordance with some embodiments, the flexible guide 211 is formed from a medically inert material, i.e. a material that does not interact chemically with tissue structures of a surgical site, having a durometer hardness measure that preferably is in a range 30-60 Shore A, and that is even more preferably in a range 40-50 Shore A. Suitable materials include Silicon, TPE, TPU, Ktryton, and Viton.

Figure 12A:
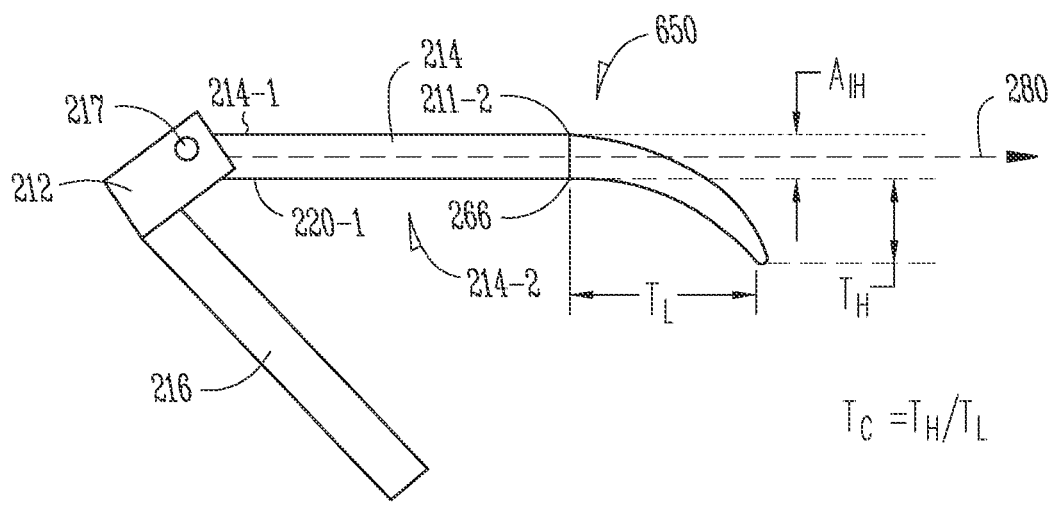
FIGS. 12A-12B are illustrative simplified schematic drawings of a side elevation view (FIG. 12A) and a top elevation view (FIG. 12B) used to explain certain relative dimensions of a stapler device having a flexible tip in accordance with some embodiments.
Figure 12B:
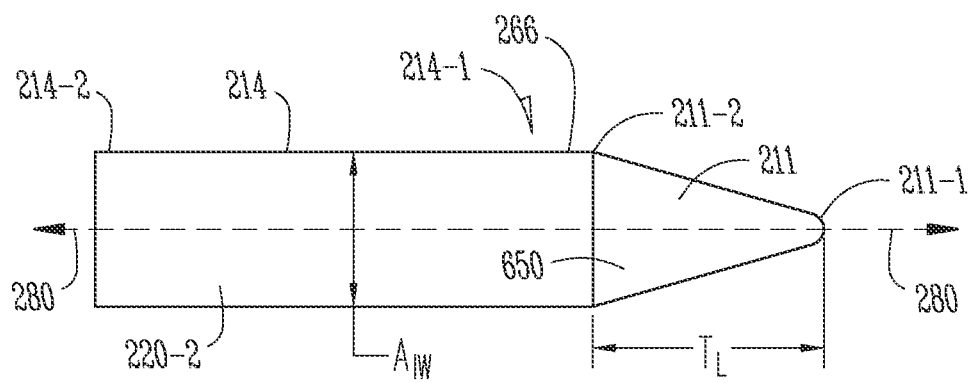

FIGS. 12A-12B are illustrative simplified schematic drawings of a side elevation view (FIG. 12A) and a top elevation view (FIG. 12B) used to explain certain relative dimensions of a stapler device 210 having a flexible tip 211 in accordance with some embodiments. Referring to FIG. 12A, the pivot 217 rotatably secures the first jaw 214 to the base 212. The second jaw 216 is fixedly secured to the base 212. The jaws 214, 216 are shown in an open position. Referring to FIGS. 12A-6B, the first jaw 214 and the flexible guide 211 share a longitudinal central axis 280.

A flexible tip length ($T_L$) refers to a length along the central axis 280 between a length between the proximal base portion 211-2 and the distal tip portion 211-1 of the flexible tip 211. A flexible tip height ($T_H$) refers to a transverse length, perpendicular to the central axis 280, between an upper portion 650 of the proximal base portion 211-2 and the distal tip portion 211-1 of the flexible guide 211. The upper portion 650 of the proximal base portion 211-2 is disposed 1s adjacent a back side surface 220-2 of the first jaw 214 that faces away from the anvil surface 220-1 when the flexible guide 211 is secured to the first jaw 214. A flexible tip curvature ($T_C$) is defined as the ratio of tip height to tip length ($T_H/T_L$). In accordance with some embodiments, the first jaw 214 has a generally rectangular shape in which a first jaw length dimension extends parallel to the longitudinal axis 280 and a first jaw width dimension extends perpendicular to the longitudinal axis 280. Thus, a first jaw width dimension (Al$_W$) refers to a transverse distance, perpendicular to the central axis 280, in a plane of the anvil surface 220-1. Moreover, a first jaw height (Al$_H$) refers to a distance between the anvil surface 220-1 and the back side surface 220-2 of the first jaw 214. Thus, the first jaw height dimension extends perpendicular to the length and width dimensions and perpendicular to the central axis 280.

FIGS. 13A-13E are illustrative drawings of multiple alternative flexible guide tips having different contours that may be interchangeably secured to a far distal end portion 266 of the first jaw 214 in accordance with some embodiments. The flexible guide tips 602-606 of FIGS. 13A-13C have different lengths and similar gentle curvatures. The flexible guide tip 608 of FIGS. 13D-13E illustrates flexure of the flexible tip 608 upon contact with tissue structure. Each of the example curvatures extends in a direction toward the second jaw 216 and within the diameter of the device from the second jaw 216 and toward from the anvil surface 220-1. Each of the alternative flexible tips 602-608 includes a beam 274 and flange 276 for use for selective engagement with the distal portion 214-1 of the first jaw 214. Different length guide tips 608-608 are suitable for different surgical settings. The wider the tissue structure behind which the first jaw 214 must pass, the longer the flexible tip that may be employed. In particular, for example, a surgeon may look for the tip to emerge from behind the tissue structure as an indication that a passage exists behind the structure through which the first jaw 214 can safely pass. The wider the tissue structure, the longer the tip that may be used.

Referring to FIGS. 13A-13C, respective first, second and third flexible tips 602, 604, 606 each has a progressively longer flexible tip length (T$_L$) and each has a progressively shallower flexible tip curvature (T$_C$). However, each has the substantially the same flexible tip height (T$_H$). In accordance with some embodiments, the flexible tip height (T$_H$) is selected to be at least as great as the first jaw height (Al$_H$) so that each of the first, second and third flexible tips 602-606 is suitable for use to explore for voids between anatomical structures (not shown) that are sufficiently wide to accommodate passage of the first jaw height (Al$_H$) dimension. The different length first, second and third flexible tips 602-606 are suitable for different exploring different length passages between anatomical structures (not shown). Moreover, the greater a flexible tip's length dimension (T$_L$) for a given flexible tip height (T$_H$), the more pliant its distal tip portion 211-1 it will be narrower at its distal tip portion 211-1, and therefore, will include less mass and will more easily comply with tissue structures (not shown) that may be encountered during traversal of an anatomical tissue region.

Figure 14A:
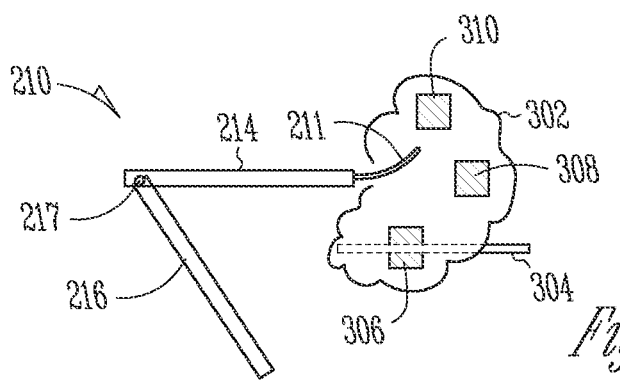
FIGS. 14A-14D are illustrative schematic diagrams showing use of a flexible guide tip to guide an anvil jaw of a stapler device among anatomical structures in accordance with some embodiments.
Figure 14B:
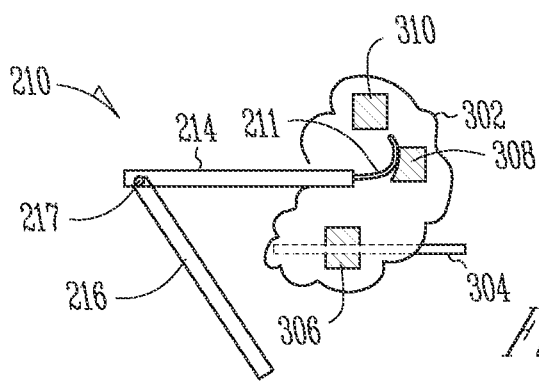
Figure 14C:
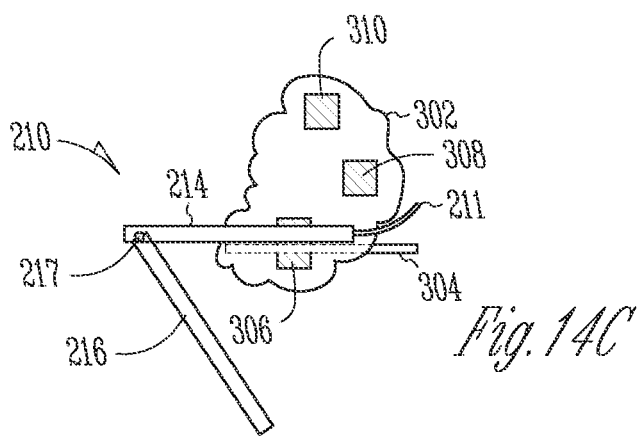
Figure 14D:
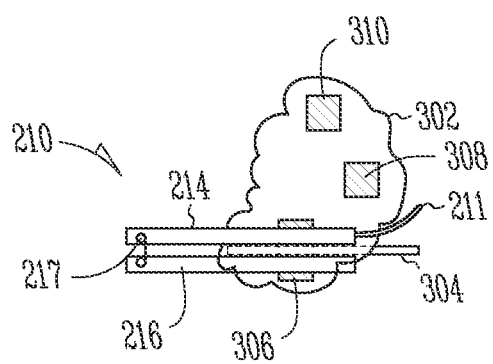

FIGS. 14A-141) are illustrative schematic diagrams showing use of a flexible guide tip to guide an anvil jaw of a stapler device among anatomical structures in accordance with some embodiments, FIG. 14A shows the stapler jaws 214, 216 in an open position, with the flexible guide 211 extending behind a large tissue structure 302, such as lung tissue for example, so as to be out of view from a perspective of a surgeon (not shown). A region that is to be stapled, referred to as a staple target region 304, indicated with dashed lines. First second and third individual anatomical structures 306, 308, 310 are disposed nearby the staple target region 304. For example, the first individual structure 306 may be a pulmonary artery; the second individual structure 308 may be a pulmonary vein; and the third individual structure 310 may be a main artery. In this example, the staple target region 304 crosses over the first individual anatomical structure 306. Referring to FIG. 14B, it is assumed that the surgeon has caused the first arm 214 and the flexible guide 211 to follow a path behind the large tissue structure 302 in which the guide 211 abuts the second individual anatomical structure 308. However, the flexible guide 211 is sufficiently flexible that its shape bends in compliance with the shape of the second individual anatomical structure 308 that it has bumped into. Although the second anatomical structure 308 is shown to have been slightly deformed due to the contact, it is not deformed sufficiently to cause damage to it. Assume that the surgeon recognizes that the guide 211 must have contacted an unseen anatomical structure, since the guide 211 has not emerged from behind the large tissue structure 302, even though it should have based upon how much of the tip's length is hidden behind it. Referring to FIG. 14C, the surgeon it is assumed that the surgeon now has inserted the anvil jaw 214 and the guide 211 behind the large tissue structure, but this time on a different path that threads between the hidden anatomical tissue structures 306-310. The tip is shown poking out from a side of the large tissue structure 302 that is opposite the side that it went in. The surgeon determines that the first jaw 214 is properly aligned with the staple target region 304. Referring to FIG. 14D, the jaws 214, 216 are rotated to a closed position clamping the staple target region 304 between them, and the staples are dispensed.

Figure 15:
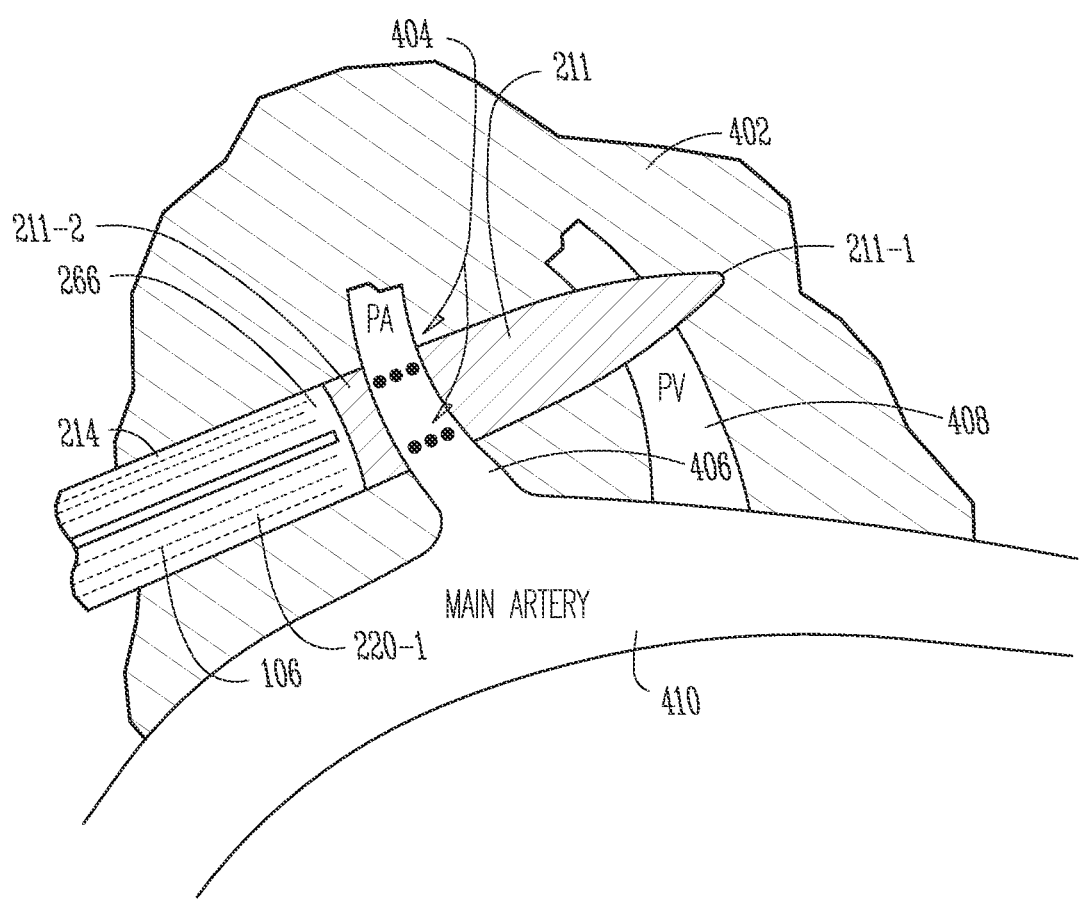
FIG. 15 is an illustrative drawing showing a flexible tip used to guide an anvil jaw between anatomical structures in accordance with some embodiments.

FIG. 15 is an illustrative drawing showing a flexible guide 211 used to guide an anvil jaw 214 between anatomical structures in accordance with some embodiments. Assume that a large tissue structure 402 hides the flexible guide 211 and the distal portion of the anvil jaw 214 from a surgeon's field view. Assume that the large tissue structure includes ling tissue and that hidden behind it are a pulmonary artery 406, a pulmonary vein 408 and a main artery 410, Further assume that a staple target region 404 indicated by dashed lines is disposed on the pulmonary artery 406. It can be seen that the guide 211 has passed behind the pulmonary artery 406 and in front of the pulmonary vein 408. The guide 211 is used by a surgeon to guide the anvil jaw, which follows behind it into position to dispense staples at the staple target region 404.

The foregoing description and drawings of embodiments in accordance with the present invention are merely illustrative of the principles of the invention. Therefore, it will be understood that various modifications can be made to the embodiments by those skilled in the art without departing from the spirit and scope of the invention, which is defined in the appended claims.

The invention claimed is:

1. A method comprising:
   receiving user input at an input control device to cause a first movement of a first jaw from a first location within the surgical site at a first side of a tissue structure toward a second side of the tissue structure within a surgical site, the first jaw including a proximal end portion and a distal end portion, the distal end portion of the first jaw having a flexible guide secured thereto, the flexible guide having an extended shape and including a base portion coupled to a distal end portion of the first jaw and a tip portion distally spaced apart from the distal end portion of the first jaw;
   positioning an endoscope to capture images to provide a surgeon's view of the tissue structure at the surgical site, for display at a display system, such that the tissue structure obscures the tip portion behind the tissue structure during the first movement from the first side of the tissue structure toward the second side of the tissue structure;

the flexible guide changing to a bended shape, in response to the tip portion contacting the tissue structure during the first movement, by increasingly bending with decreasing distance between the first jaw and the anatomical structure, to protect the anatomical structure from damage;

using the display system to display images that show the tissue structure obscuring the flexible guide during the first movement and to display images that show the flexible guide unobscured by the tissue structure when the flexible guide reaches the second side of the tissue structure; and in response to the images displayed at the display system showing the flexible guide unobscured by the tissue structure when the flexible guide reaches the second side of the tissue structure, receiving user input at an input control device to cause a second jaw, pivotally mounted at a pivot axis at the proximal end portion of the first jaw, to rotate about the pivot axis to capture staple target tissue structure between the first jaw and the second jaw.

2. The method of claim 1 further including:
injecting staples to the tissue structure captured between the first jaw and the second jaw.

3. The method of claim 1, further including:
injecting staples from the second jaw to the tissue structure captured between the first jaw and the second jaw.

4. The method of claim 1 further including:
using the endoscope to capture images to provide the surgeon's view of the tissue structure at the surgical site before the tip portion reaches the first location at the first side of the tissue structure during the first movement; and using the display system to display the captured images to provide the surgeon's view of the tissue structure at the surgical site before the tip portion reaches the first location at the first side of the tissue structure during the first movement.

5. The method of claim 1,
wherein the first movement is in a direction parallel to a longitudinal central axis of the first jaw, the longitudinal central axis extending between the proximal end portion of the first jaw and the distal end portion of the first jaw.

6. The method of claim 1,
in response to the base portion of the guide contacting the anatomical structure, the flexible guide stops increasingly bending toward the proximal end portion of the first jaw with decreasing distance between the first jaw and the tissue structure.

7. The method of claim 1,
wherein the flexible guide having a curved extended shape.

8. The method of claim 1,
wherein in response to the tip portion contacting the anatomical structure during the first movement, the flexible guide changing to the bended shape by increasingly bending toward the proximal end portion of the first jaw with decreasing distance between the first jaw and the tissue structure, during the first movement.

9. The method of claim 1 further including:
in response to the tip portion contacting the anatomical structure during the first movement, receiving user input at an input control device to cause a second movement of the first jaw parallel to the longitudinal central axis of the first jaw away from the first location at the first side of a tissue structure within the surgical site;

in response to the second movement, the tip portion unbending to return to the extended shape;

receiving user input at an input control device to cause a third movement of the first jaw from a second location within the surgical site at the first side of the tissue structure toward the second side of the tissue structure within the surgical site;

in response to the tip portion contacting the anatomical structure during the third movement, the flexible guide changing to a bended shape by increasingly bending with decreasing distance between the first jaw and the tissue structure, during the movement of the first jaw toward the second location at the first side of the tissue structure; and using the display system to display the images to provide the surgeon's view of the tissue structure at the surgical site captured using the endoscope, to indicate to the user whether the flexible guide reached the second side of the tissue structure without contacting the anatomical structure.

10. The method of claim 9,
in response to the display system indicating to the user that the flexible guide reached the second side of the tissue structure without contacting the anatomical structure, receiving user input at the input control device to cause the second jaw, pivotally mounted at a pivot axis at the proximal end portion of the first jaw, to rotate about the pivot axis to capture the staple target tissue structure between the first jaw and the second jaw.

11. The method of claim 9 further including:
using the endoscope to capture the images to provide the surgeon's view of the tissue structure the surgical site before the tip portion reaches the second location at the first side of the tissue structure during the third movement; and using the display system to display the captured images to provide the surgeon's view of the tissue structure the surgical site before the tip portion reaches the second location at the first side of the tissue structure during the third movement.

12. The method of claim 9,
wherein the third movement is in a direction parallel to a longitudinal central axis of the first jaw.

13. The method of claim 9,
in response to the base portion of the guide contacting the anatomical structure, the flexible guide stops increasingly bending toward the proximal end portion of the first jaw with decreasing distance between the first jaw and the tissue structure.

* * * * *